United States Patent
Al-Jilaihawi et al.

(10) Patent No.: US 10,543,078 B2
(45) Date of Patent: Jan. 28, 2020

(54) MODULAR DIS-ASSEMBLY OF TRANSCATHETER VALVE REPLACEMENT DEVICES AND USES THEREOF

(71) Applicant: Cedars-Sinai Medical Center, Los Angeles, CA (US)

(72) Inventors: Hasanian Al-Jilaihawi, West Hollywood, CA (US); Rajendra Makkar, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 15/023,995

(22) PCT Filed: Oct. 16, 2014

(86) PCT No.: PCT/US2014/060957
§ 371 (c)(1),
(2) Date: Mar. 22, 2016

(87) PCT Pub. No.: WO2015/057995
PCT Pub. Date: Apr. 23, 2015

(65) Prior Publication Data
US 2016/0228241 A1 Aug. 11, 2016

Related U.S. Application Data

(60) Provisional application No. 61/891,826, filed on Oct. 16, 2013.

(51) Int. Cl.
*A61F 2/24* (2006.01)
(52) U.S. Cl.
CPC .......... *A61F 2/2409* (2013.01); *A61F 2/2427* (2013.01); *A61F 2/2433* (2013.01);
(Continued)

(58) Field of Classification Search
CPC .... A61F 2/2409; A61F 2/2412; A61F 2/2427; A61F 2/2433; A61F 2250/0098;
(Continued)

(56) References Cited

U.S. PATENT DOCUMENTS 4,694,838 A 9/1987 Wijayarthna et al.
4,738,667 A 4/1988 Galloway
(Continued)

FOREIGN PATENT DOCUMENTS

CN 1106647 A 8/1995
CN 1647777 A 8/2005
(Continued)

OTHER PUBLICATIONS

PCT/US2014/060526 International Preliminary Report on Patentability dated Apr. 19, 2016, 7 pages.
(Continued)

*Primary Examiner* — Eric J Rosen
*Assistant Examiner* — Brooke Labranche
(74) *Attorney, Agent, or Firm* — Nixon Peabody LLP (57) ABSTRACT

The present invention provides modular transcatheter valve replacement devices and methods of using the same to treat valvular heart diseases. Disclosed is a bottom module that contains a heart valve replacement, and a top module connected to the bottom module. The top module may be bio-absorbable, or may contain one or more severable joints that allow the top module to be removed after implantation. The removable or absorbable top portion serves to add additional length the structure to add in orientation during implantation, but is removed or absorbed to minimize the metal and other foreign material in a patient's body that could cause thrombosis or other reactions.

13 Claims, 5 Drawing Sheets

(52) U.S. Cl.
CPC ............... *A61F 2210/0004* (2013.01); *A61F 2210/0071* (2013.01); *A61F 2220/0025* (2013.01); *A61F 2250/0031* (2013.01); *A61F 2250/0098* (2013.01); *A61F 2310/00023* (2013.01); *A61F 2310/00041* (2013.01); *A61F 2310/00149* (2013.01); *A61F 2310/00155* (2013.01)

(58) Field of Classification Search
CPC ...... A61F 2220/0025; A61F 2210/0004; A61F 2310/00155; A61F 2310/00149; A61F 2210/0071; A61F 2250/0031; A61F 2250/0071; A61F 2310/00023; A61F 2310/00041
See application file for complete search history.

(56) References Cited

U.S. PATENT DOCUMENTS

| | | | |
|---|---|---|---|
| 5,423,829 A | 6/1995 | Pham et al. |
| 5,833,632 A | 11/1998 | Jacobsen et al. |
| 5,964,744 A | 10/1999 | Balbierz et al. |
| 5,964,797 A | 10/1999 | Ho |
| 5,972,019 A | 10/1999 | Engleson et al. |
| 6,059,779 A | 5/2000 | Mills |
| 6,086,557 A | 7/2000 | Morejohn et al. |
| 6,217,611 B1 | 4/2001 | Klostermeyer |
| 6,287,277 B1 | 9/2001 | Yan |
| 6,350,282 B1 | 2/2002 | Eberhardt |
| 6,589,230 B2 | 7/2003 | Gia et al. |
| 6,953,473 B2 | 10/2005 | Porter |
| 6,964,657 B2 | 11/2005 | Cragg et al. |
| 6,976,965 B2 | 12/2005 | Corl et al. |
| 7,134,994 B2 | 11/2006 | Alpert et al. |
| 7,340,288 B1 | 3/2008 | Karicherla et al. |
| 7,935,144 B2 | 5/2011 | Robin et al. |
| 8,070,800 B2 | 12/2011 | Lock et al. |
| 8,092,524 B2 | 1/2012 | Nugent et al. |
| 8,372,069 B2 | 2/2013 | Kassab |
| 8,377,112 B2 | 2/2013 | Griffin et al. |
| 8,408,214 B2 | 4/2013 | Spenser |
| 8,430,927 B2 | 4/2013 | Bonhoeffer |
| 8,491,648 B2 | 7/2013 | Hassan et al. |
| 2002/0169474 A1 | 11/2002 | Kusleika et al. |
| 2004/0073141 A1 | 4/2004 | Hartley et al. |
| 2004/0172081 A1 | 9/2004 | Wang |
| 2005/0203425 A1 | 9/2005 | Langston |
| 2005/0240200 A1 | 10/2005 | Bergheim |
| 2005/0256566 A1 | 11/2005 | Gabbay |
| 2005/0267010 A1 | 12/2005 | Goodson et al. |
| 2006/0064114 A1 | 3/2006 | Obitsu et al. |
| 2006/0155305 A1 | 7/2006 | Freudenthal |
| 2006/0287719 A1 | 12/2006 | Rowe et al. |
| 2007/0050021 A1 | 3/2007 | Johnson |
| 2007/0203562 A1 | 8/2007 | Malewicz et al. |
| 2008/0027334 A1 | 1/2008 | Langston |
| 2008/0033467 A1 | 2/2008 | Miyamoto et al. |
| 2008/0183273 A1 | 7/2008 | Mesana et al. |
| 2008/0221551 A1 | 9/2008 | Goodson et al. |
| 2008/0306499 A1 | 12/2008 | Katoh et al. |
| 2008/0319541 A1 | 12/2008 | Filsoufi |
| 2009/0082678 A1 | 3/2009 | Smith |
| 2009/0248143 A1 | 10/2009 | Laham |
| 2009/0259292 A1 | 10/2009 | Bonhoeffer |
| 2009/0276040 A1 | 11/2009 | Rowe et al. |
| 2010/0030330 A1 | 2/2010 | Bobo et al. |
| 2010/0076549 A1 | 3/2010 | Keidar et al. |
| 2010/0094209 A1 | 4/2010 | Drasler et al. |
| 2010/0121434 A1* | 5/2010 | Paul .................... A61F 2/24 623/2.11 |
| 2010/0168840 A1 | 7/2010 | Kassab |
| 2010/0185275 A1 | 7/2010 | Richter et al. |
| 2010/0191272 A1 | 7/2010 | Keating |
| 2010/0211094 A1 | 8/2010 | Sargent |
| 2010/0331948 A1 | 12/2010 | Turovskiy et al. |
| 2011/0137397 A1 | 6/2011 | Chau et al. |
| 2012/0059458 A1 | 3/2012 | Buchbinder et al. |
| 2012/0130230 A1 | 5/2012 | Eichler et al. |
| 2012/0158129 A1 | 6/2012 | Duffy et al. |
| 2012/0283757 A1* | 11/2012 | Miller ............... A61B 17/0401 606/151 |
| 2012/0283812 A1 | 11/2012 | Lagodzki et al. |
| 2012/0283820 A1 | 11/2012 | Tseng et al. |
| 2012/0310328 A1* | 12/2012 | Olson ..................... A61F 2/07 623/1.26 |
| 2012/0310330 A1 | 12/2012 | Buchbinder et al. |
| 2013/0090726 A1 | 4/2013 | Rowe et al. |
| 2013/0109960 A1 | 5/2013 | Stinis |
| 2013/0116779 A1 | 5/2013 | Weber |
| 2013/0166017 A1* | 6/2013 | Cartledge ............... A61F 2/93 623/1.15 |
| 2013/0190857 A1 | 7/2013 | Mitra et al. |
| 2013/0190865 A1 | 7/2013 | Anderson |
| 2013/0261738 A1 | 10/2013 | Clague et al. |
| 2013/0261739 A1 | 10/2013 | Kuehn |
| 2013/0274618 A1 | 10/2013 | Hou et al. |
| 2013/0331864 A1 | 12/2013 | Jelich et al. |
| 2013/0331921 A1 | 12/2013 | Roubin |
| 2014/0114402 A1 | 4/2014 | Ahlberg et al. |
| 2014/0171958 A1 | 6/2014 | Baig |
| 2014/0194981 A1 | 7/2014 | Menk et al. |
| 2014/0200662 A1 | 7/2014 | Eftel et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0277419 A1 | 9/2014 | Garde et al. |
| 2014/0303719 A1 | 10/2014 | Cox et al. |
| 2014/0350669 A1 | 11/2014 | Gillespie et al. |
| 2016/0206424 A1 | 7/2016 | Al-Jilaihawi et al. |
| 2016/0228013 A1 | 8/2016 | Al-Jilaihawi et al. |
| 2016/0235422 A1 | 8/2016 | Al-Jilaihawi et al. |
| 2016/0302920 A1 | 10/2016 | Al-Jilaihawi |
| 2016/0310699 A1 | 10/2016 | Al-Jilaihawi |
| 2018/0078363 A1 | 3/2018 | Al-Jilaihawi |

FOREIGN PATENT DOCUMENTS

| | | |
|---|---|---|
| CN | 101474102 A | 7/2009 |
| CN | 101489504 A | 7/2009 |
| CN | 101947146 A | 1/2011 |
| CN | 101972177 A | 2/2011 |
| CN | 103237523 A | 8/2013 |
| CN | 104220028 A | 12/2014 |
| CN | 104334119 A | 2/2015 |
| CN | 105611871 A | 5/2016 |
| CN | 105611889 A | 5/2016 |
| CN | 105744969 A | 7/2016 |
| CN | 105764447 A | 7/2016 |
| CN | 107405191 A | 11/2017 |
| EP | 2732796 A1 | 5/2014 |
| EP | 3054838 A1 | 8/2016 |
| EP | 3057522 A1 | 8/2016 |
| EP | 3079633 A1 | 10/2016 |
| EP | 3099345 A1 | 12/2016 |
| EP | 3267940 A1 | 1/2018 |
| WO | 1996017644 A1 | 6/1996 |
| WO | 1998048879 | 11/1998 |
| WO | 99/15223 A1 | 4/1999 |
| WO | 99/15227 A1 | 4/1999 |
| WO | 1999015223 A1 | 4/1999 |
| WO | 0249511 A1 | 6/2002 |
| WO | 2005059379 A1 | 6/2005 |
| WO | 2007081820 A1 | 7/2007 |
| WO | 2010085659 A1 | 7/2010 |
| WO | 2011039091 A1 | 4/2011 |
| WO | 2012009675 A2 | 1/2012 |
| WO | 2012161769 A1 | 11/2012 |
| WO | 2012/173697 A1 | 12/2012 |
| WO | 2013061281 A1 | 5/2013 |
| WO | 2014145469 A1 | 9/2014 |
| WO | 2015/054296 A1 | 4/2015 |
| WO | 2015/057735 A1 | 4/2015 |
| WO | 2015/057995 A2 | 4/2015 |

(56) References Cited

FOREIGN PATENT DOCUMENTS

| WO | 2015/058001 A1 | 4/2015 |
|---|---|---|
| WO | 2015/089334 A1 | 6/2015 |
| WO | 2015/117025 A1 | 8/2015 |
| WO | 2016145250 A1 | 9/2016 |

OTHER PUBLICATIONS

PCT/US2014/060966 International Preliminary Report on Patentability dated Apr. 19, 2016, 6 pages.
Extended European Search Report for EP Application No. 14853895.2 dated May 10, 2017, 8 pages.
Partial Supplementary European Search Report for EP Application No. 14851950.7 dated Apr. 10, 2017, 6 pages.
Extended European Search Report for EP Application No. 14869869.9 dated May 4, 2017, 7 pages.
PCT/US2016/021866 International Search Report and Written Opinion dated May 23, 2016, 11 pages.
PCT/US2014/069849 International Preliminary Report on Patentability dated Jun. 14, 2016; 7 pages.
PCT/US2015/013956 International Preliminary Report on Patentability dated Aug. 2, 2016; 7 pages.
PCT/US2014/059547 International Preliminary Report on Patentability dated Apr. 12, 2016; 6 pages.
PCT/US2014/060526 International Search Report and Written Opinion dated Feb. 10, 2015; 7 pages.
PCT/US2014/060957 International Search Report and Written Opinion dated Apr. 1, 2015; 10 pages.
PCT/US2014/060966 International Search Report and Written Opinion dated Jan. 29, 2015; 6 pages.
PCT/US2014/059547 International Search Report and Written Opinion dated Mar. 3, 2015; 9 pages.
PCT/US2014/069849 International Search Report and Written Opinion dated Mar. 2, 2015; 8 pages.
PCT/US2015/013956 International Search Report and Written Opinion dated Jun. 26, 2015; 10 pages.
Astarci et al. Transapical explantation of an embolized transcatheter valve. Interact Cardiovasc Thorac Surg (2011). 13:1-2.
Blows et al. The pressure wire in practice. Heart (2007). 93:419-422.
Bonhoeffer et al. The multi-track angiography catheter: a new tool for complex catheterisation in congenital heart disease. Heart (1996). 76:173-177.
Chiam et al. Percutaneous Transcatheter Mitral Valve Repair. J Am Coll Cardiol (2011). 4(1):1-13.
Ho, S.Y. Structure and anatomy of the aortic root. Eur J Echocardiogr (2009). 10:i3-i10.
Jolicoeur et al. Tiara: A Novel Catheter-Based Mitral Valve Bioprosthesis Initial Experiments and Short-Term Pre-Clinical Results. J Am Coll Cardiol (2012). 60(15):1430-1431.
Lange et al. Diagnostic Cardiac Catheterization. Circulation (2003). 107:e111-e113.
Masson et al. Percutaneous Treatment of Mitral Regurgitation. Circ Cardiovasc Interv (2009): 2:140-146.
McCarthy et al. Anatomy of the mitral valve: understanding the mitral valve complex in mitral regurgitation. Eur J Echocardiogr (2010). 11:i3-i9.
Ormiston et al. Bioabsorbable Coronary Stents (2009). Circ Cardiovasc Interv (2009). 2:255-260.
Sievers et al. The everyday used nomenclature of the aortic root components: the tower of Babel? Eur J Cardio-Thorac Surg (2011). 0:1-5.
Sinning et al. Aortic Regurgitation Index Defines Severity of Peri-Prosthetic Regurgitation and Predicts Outcome in Patients After Transcatheter Aortic Valve Implantation. J Am Coll Cardiol (2012). 59(13):1134-1141.
Tonino et al. Fractional Flow Reserve versus Angiography for Guiding Percutaneous Coronary Intervention. New Engl J Med (2009). 360(3):213-224.
Tsai et al. Transcatheter Retrieval of Dislodged Port-A Catheter Fragments: Experience with 47 Cases. Acta Cardiol Sin (2006). 22:221-228.
Van Mieghem et al. Anatomy of the Mitral Valvular Complex and Its Implications for Transcatheter Interventions for Mitral Regurgitation. J Am Coll Cardiol (2010). 56(8):617-626.
PCT/US2014/060957 International Preliminary Report on Patentability dated Apr. 28, 2016; 10 pages.
PCT/US2016/021866 International Preliminary Report on Patentability dated Sep. 21, 2017, 9 pages.
EP16762555.7 Supplementary European Search Report dated Oct. 5, 2018, 8 pages.
Crushing. (n.d.) American Heritage Dictionary of the English Language, Fifth Edition, 2011, retrieved from https://thefreedictionary.com/crushing.
Compress. (n.d.) Merriam-Webster, 2018, retrieved from https://www.merriam-webster.com/dictionary/compress.
EP 14851950.7 Extended European Search Report dated Jul. 12, 2017, 10 pages.
EP 14851950.7 Examination Report dated May 24, 2018, 4 pages.
EP 14869869.9 Examination Report dated Jan. 23, 2019, 4 pages.
EP 15743048.9 Extended Search Report dated Aug. 24, 2017, 8 pages.

* cited by examiner

MODULAR DIS-ASSEMBLY OF TRANSCATHETER VALVE REPLACEMENT DEVICES AND USES THEREOF

CROSS-REFERENCE TO RELATED APPLICATIONS

This application is a National Phase of International Application No. PCT/US2014/060957 filed Oct. 16, 2014, currently pending, which designated the U.S. and that International Application was published under PCT Article 21(2) in English, which also includes a claim of priority under 35 U.S.C. § 119(e) to U.S. provisional patent application No. 61/891,826 filed Oct. 16, 2013, the entirety of which is hereby incorporated by reference.

FIELD OF INVENTION

Provided herein are modular transcatheter valve replacement devices and methods of using the same to optimize valve replacement of a diseased heart valve.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Valvular heart disease is characterized by damage to or a defect in one of the four heart valves: the mitral, aortic, tricuspid or pulmonary. The mitral and tricuspid valves control the flow of blood between the atria and the ventricles (the upper and lower chambers of the heart). The pulmonary valve controls the blood flow from the heart to the lungs, and the aortic valve governs blood flow between the heart and the aorta, and thereby to the blood vessels in the rest of the body. The mitral and aortic valves are most frequently affected by valvular heart disease. Transcatheter valve therapies are one treatment option for patients. For example, transcatheter aortic valve replacement (TAVR—also known as TAVI or transcatheter aortic valve implantation) is a procedure for select patients with severe symptomatic aortic stenosis (narrowing of the aortic valve opening) who are not candidates for traditional open chest surgery or are high-risk operable candidates. This procedure wedges a replacement valve into the aortic valve's place without removing the old or damaged valve. A replacement valve is inserted percutaneously using a catheter and implanted in the orifice of the native aortic valve. Replacement valves may be artificial (prosthetic valves) or made from animal tissue (bioprosthetic valves). The type of replacement valve selected depends on the patient's age, condition, and the specific valve affected.

Certain minimum height or length (the longitudinal length along the flow axis of the valve) of the TAVR device is required to optimally orient the device in the aortic canal during deployment of a TAVR device. The longer the TAVR device, the easier it is to position in the canal of the aortic valve. However, the longer the TAVR device, the more metal that remains within the body, which may cause additional complications and reactions including thrombus formation.

To solve these technical issues pertaining to the TAVR procedure, the inventors developed modular transcatheter valve replacement devices. In some embodiments, the modular transcatheter valve comprises a top (aortic aspect) module and a bottom (ventricular aspect) module. The bottom module is a small replacement valve (prosthetic or bioprosthetic) that sits in a patient's heart permanently to replace a diseased valve. The top module is a temporary component that increases the length of the bottom module for easy handling and optimal positioning. The top module may be mechanically detachable, electrically detachable, or bio-absorbable. The modular design maximizes ease of device positioning and minimizes the hardware left behind in the body of the subject.

SUMMARY OF THE INVENTION

The following embodiments and aspects thereof are described and illustrated in conjunction with systems, compositions and methods which are meant to be exemplary and illustrative, not limiting in scope.

In various embodiments, described herein is a device for transcatheter valve replacement. The device comprises a top module and a bottom module. The bottom module comprises a replacement heart valve. The top module is attached to the bottom module prior to deployment of the device, and then is detached from the bottom module after deployment of the device in some embodiments, or may be bio-absorbable. In some embodiments, the top module may be resemble or be configured as a stent, or may be a simple structure with a few structural wires or ribs to orient the device.

In various embodiments, provided herein is a method for transcatheter valve replacement. The method comprise the following steps: (1) providing a device, comprising a top module and a bottom module, wherein the bottom module comprises a replacement heart valve, the top module is attached to the bottom module prior to deployment of the device; (2) deploying the device in a patient's heart to replace a diseased heart valve; (3) detaching the top module from the bottom module; and (4) retrieving the top module out of the patient's heart. In some embodiments where the top module is bio-absorbable, steps (3) and (4) do not need to be performed.

In various embodiments, described herein is a device for transcatheter valve replacement. The device comprises a top module and a bottom module. The bottom module comprises a replacement heart valve. The top module is made of bio-absorbable material and is attached to the bottom module prior to deployment of the device.

In various embodiments, provided herein is a method for transcatheter valve replacement. The method comprise the following steps: (1) providing a device, comprising a top module and a bottom module, wherein the bottom module comprises a replacement heart valve, the top module is attached to the bottom module prior to deployment of the device, and the top module is made of bio-absorbable material; and (2) deploying the device in a patient's heart to replace a diseased heart valve.

In various embodiments, disclosed herein is a method of manufacturing a transcatheter valve replacement system including a top module, a bottom module, where the top module is absorbable. This method may include separate manufacturing the bottom module that incorporates a prosthetic valve, but with either a detachable joint portion to the bottom module, or some other connection that may be permanent. Further described is a method of manufacturing a top module that may include manufacturing an absorbable top module, with a detachable joint for attaching to the bottom module. In some embodiments the joint attachment may be permanent, in the case of the absorbable top module. These devices may be manufacturing according to known methods for manufacturing metal allows, shape memory metal and plastic biocompatible plastics and other materials suitable for manufacturing the devices herein.

BRIEF DESCRIPTION OF FIGURES

Exemplary embodiments are illustrated in the referenced figures. It is intended that the embodiments and figures disclosed herein are to be considered illustrative rather than restrictive.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russell, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Figure 1A:
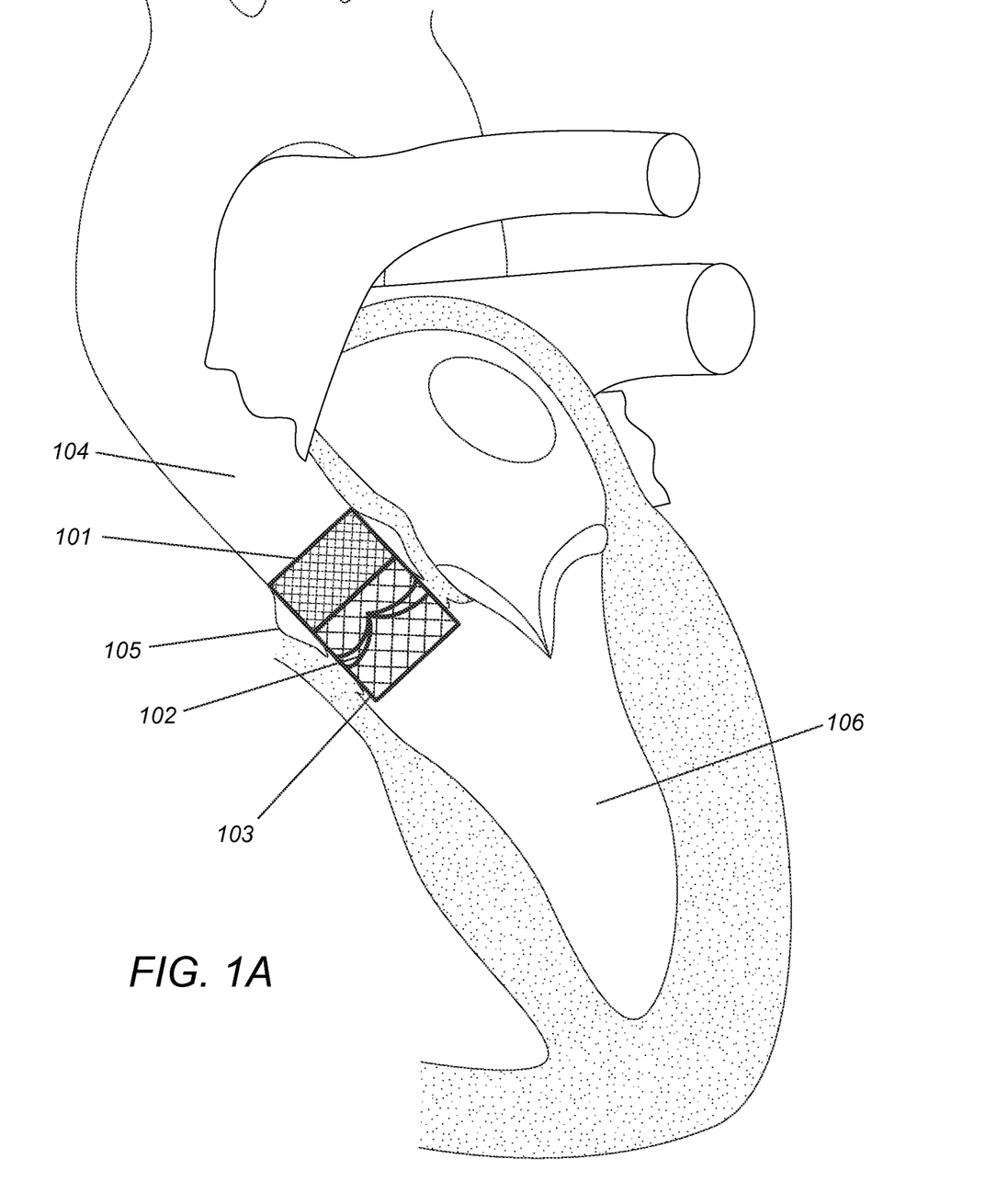
FIG. 1A depicts, in accordance with various embodiments of the present invention, a cross sectional view of a modular transcatheter valve replacement device used in TAVR including a top module and a bottom module as implanted into aortic root.

FIG. 1A illustrates an embodiment of the valve replacement system that includes a top module 101, a bottom module 103, where the bottom module 103 includes a replacement valve. In some embodiments, the replacement valve may include leaflets 102 or valve mechanisms. FIG. 1A illustrates the device initially implanted and deployed in the aortic canal, with the ascending aorta 104 above the device, while the device is situated in the native aortic root 105, and with the left ventricle 106 below the device. After the device is implanted, the top module 101 may either be absorbed or removed.

Figure 1B:
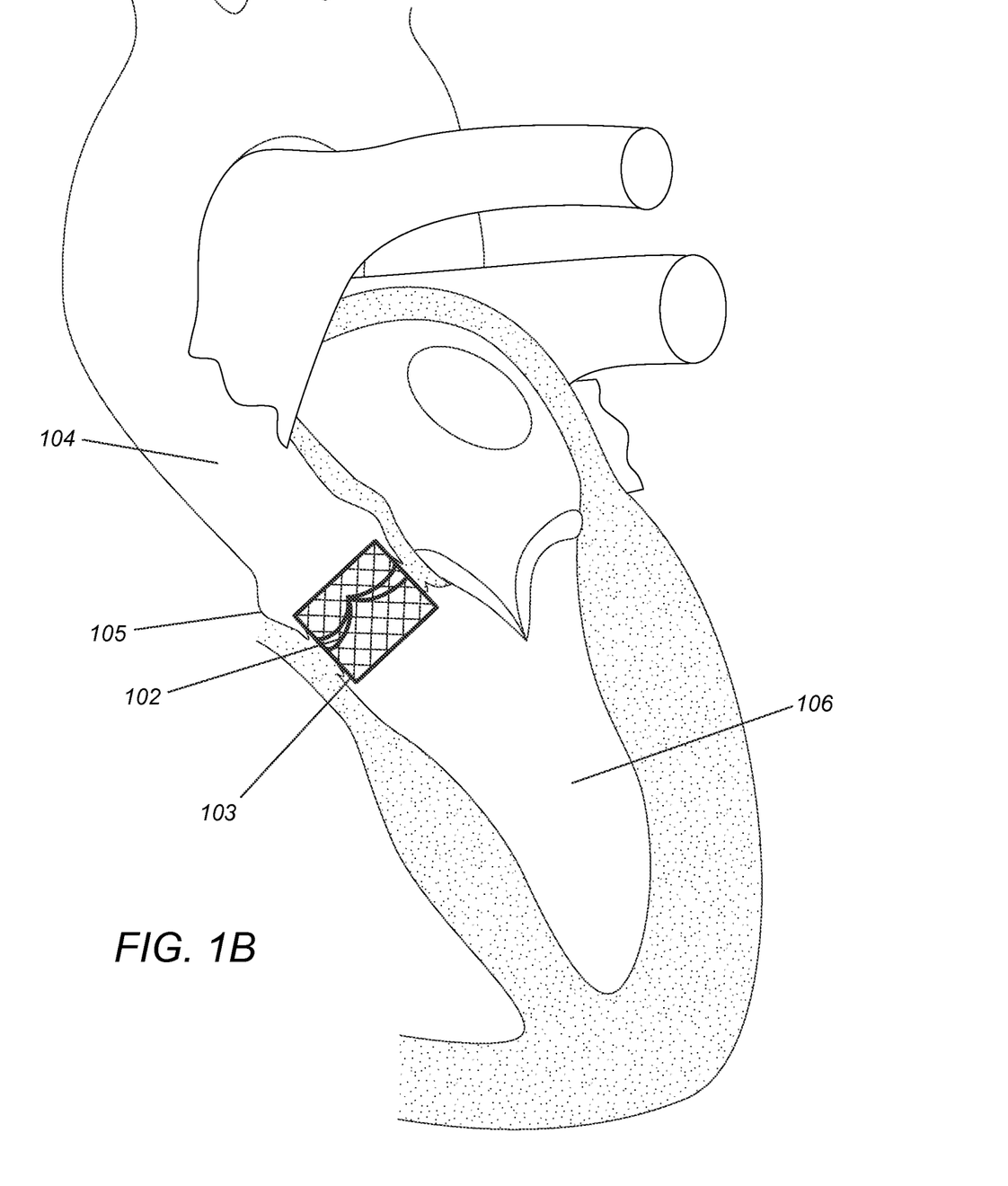
FIG. 1B depicts, in accordance with various embodiments of the present invention, a cross sectional view of a modular transcatheter valve replacement device used in TAVR, wherein a bio-absorbable or removable top module has been absorbed or removed.

FIG. 1B illustrates the bottom module 103 which contains the valve and leaflets 102 implanted in the native aortic root 105 with the top module 101 already removed or absorbed. This illustrates the reduction in metal and surface area potential for reaction with the implant that removal of the top module 101 allows. Additionally, as can be appreciated from the illustrations that positioning the bottom module 103 without the increased distance of the top module 101, would allow additional play and rotation of the bottom module, making it difficult to orient during implantation.

Figure 2A:
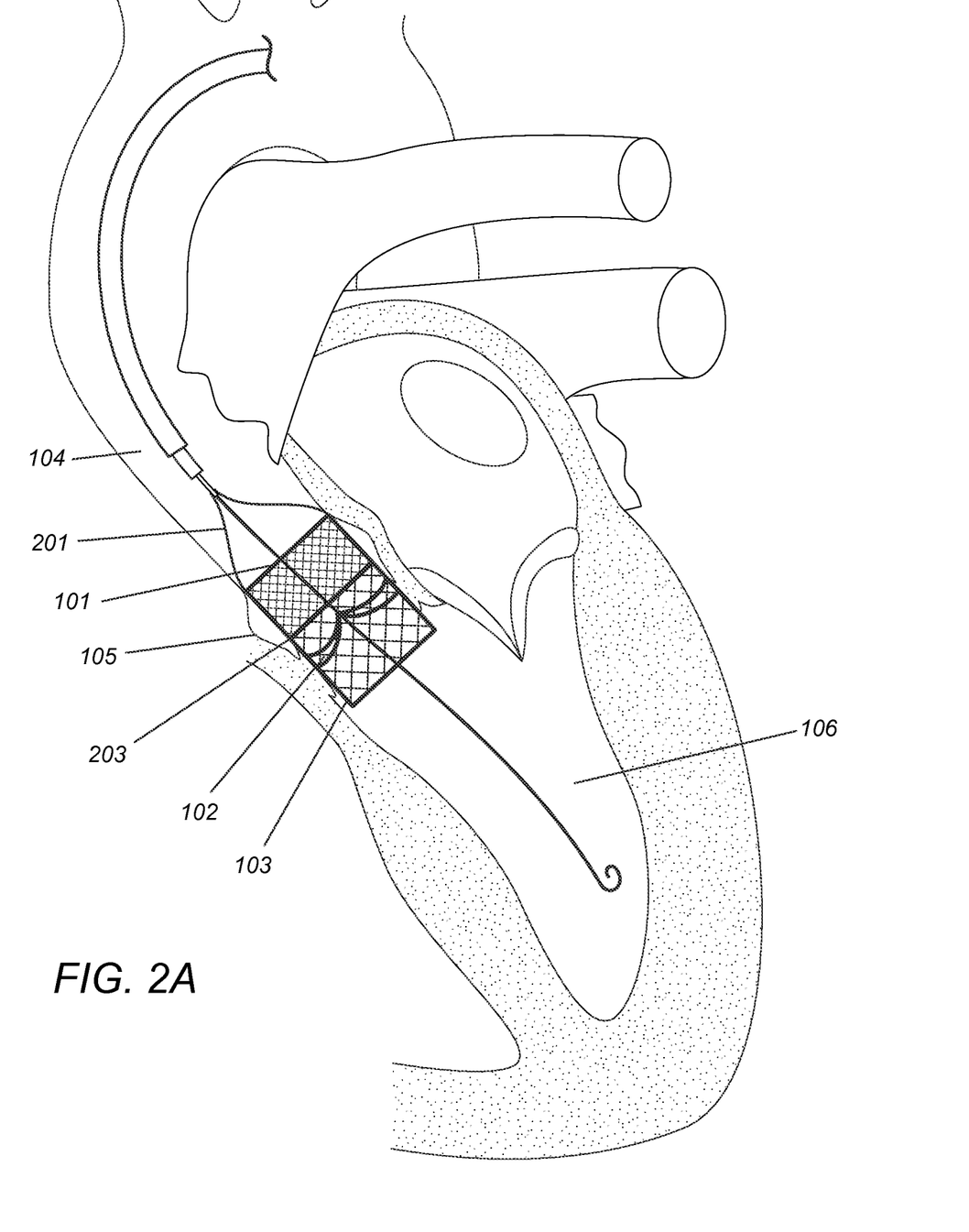
FIG. 2A depicts, in accordance with various embodiments of the present invention, a cross sectional view of a transcatheter valve replacement device with a top module and a bottom module, with retrieval cords attached to the top module.
Figure 2B:
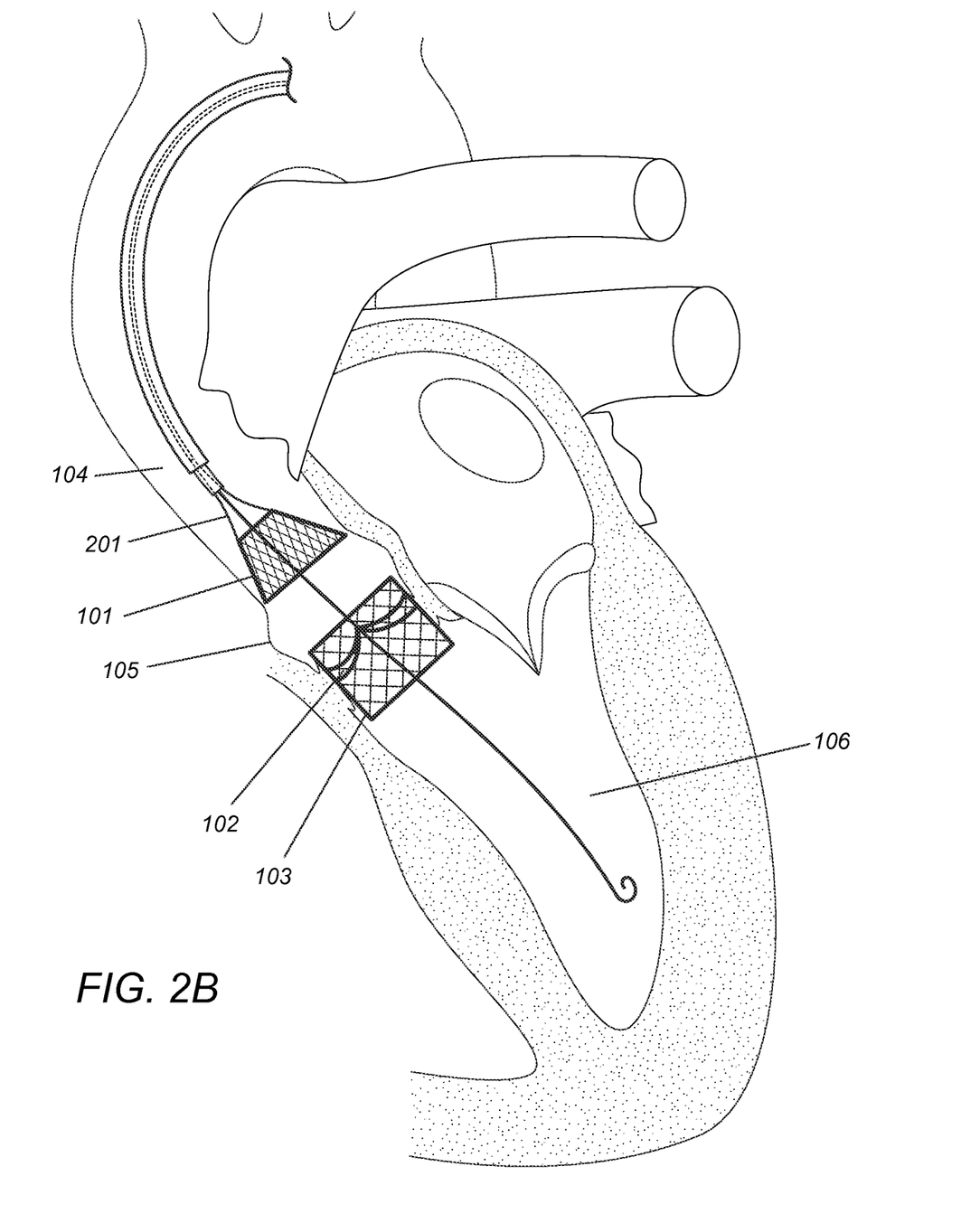
FIG. 2B depicts, in accordance with various embodiments of the present invention, a cross sectional view of a modular transcatheter valve replacement device, wherein the top module has been detached and retrieved after valve deployment, with the bottom module remaining permanently in a patient's heart.

Devices with Mechanically, Electromechanically, or Electrolytically Detachable Top Modules In various embodiments, and as illustrated in FIG. 2A, provided herein is a device for transcatheter valve replacement. The device comprises a top module 101 and a bottom module 103. The bottom module 103 comprises a replacement heart valve including, in some embodiments, leaflets 102 or other valve structures. The leaflets 102 or other valve structures may be prosthetic or bio-prosthetic. The top module 101 is attached to the bottom module 103 prior to deployment of the device. In some embodiments, and as illustrated in FIG. 2B, the top module 101 may be detached from the bottom module 103 after deployment of the device. In this embodiment and as illustrated in FIG. 2A, the top module 101 includes retrieval cords 201 that may be connected to a guide wire, catheter or other structure that may be refracted, thereby removing the top module 101. In an exemplary embodiment, the retrieval cord 201 is made of nitinol or other suitable materials. In some embodiments, the cords 201 may be attached to the top module 101 in any convenient matter, in this embodiment, they are attached so that connection point is in a center of a cross-section of the top module 101, so that retraction force will not cause the top module to rotate sideways or put uneven pressure on cardiac or body structures during removal. In some embodiments, top module 101 may be collapsible upon removal, and/or electrolytic disintegration of the detachable joint 203. Additionally, the device may contain detachable joint 203, that removably connects the top module 10 to the bottom module 103, and may be comprised of the various materials and devices disclosed herein. Accordingly, as illustrated in FIG. 2B, after the detachable joint 203 is detached, and the retrieval cords utilized to retract the top module 101, only the bottom module 103 remains implanted in the aortic canal.

Figure 2C:
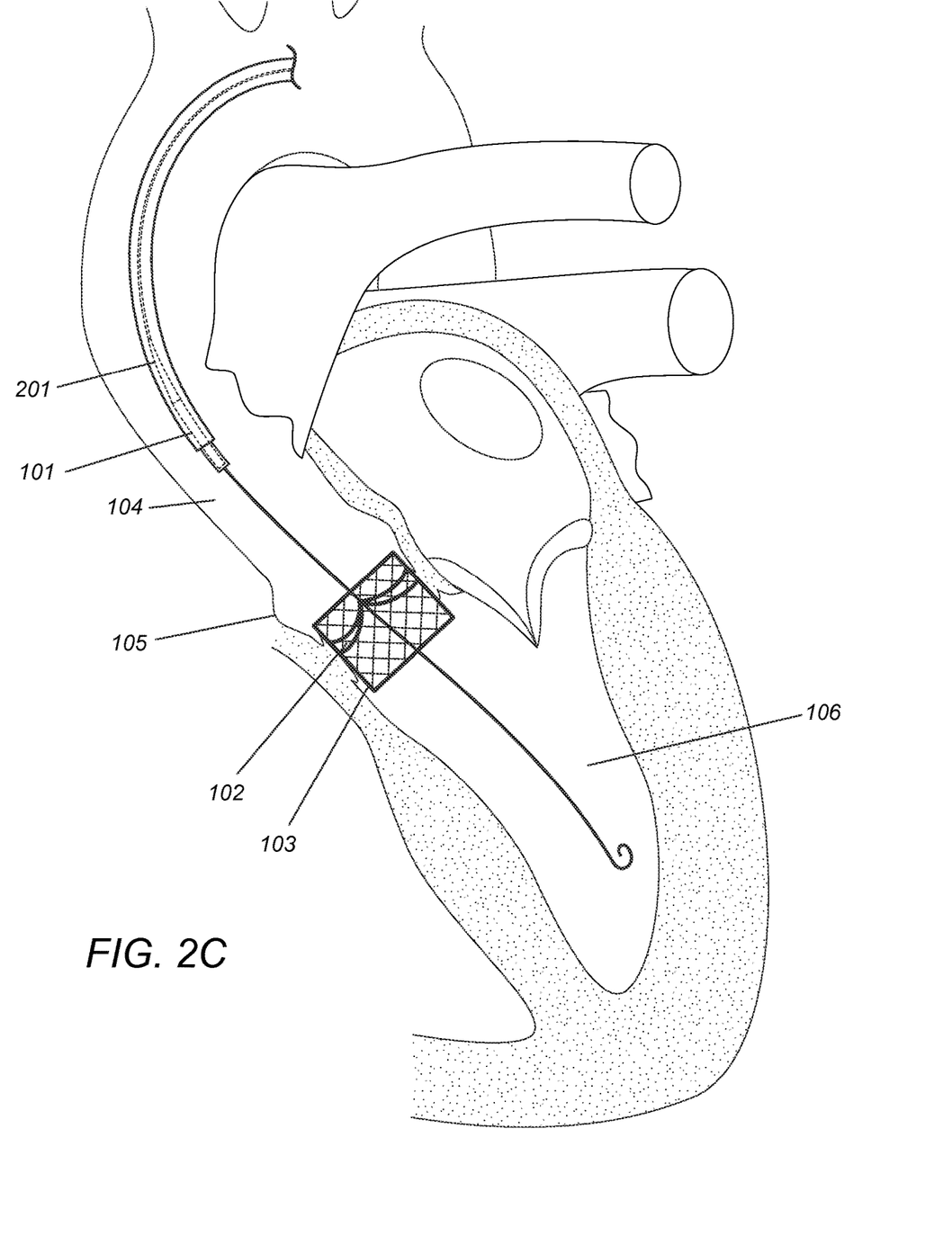
FIG. 2C depicts, in accordance with various embodiments of the present invention, a cross sectional view of a module transcatheter replacement device, wherein the top module has been detached and retrieved after valve deployment through a delivery catheter, which the bottom module remaining permanently in a patient's heart.

FIG. 2C illustrates an embodiment of the top module 101 being retrieved. In this embodiment, once the top module is detached, it must collapse to fit inside a catheter or other device. FIG. 2C shows the top module 101 and cords 201 collapsed inside of and being retrieved through a catheter. In some embodiments, disconnecting the detachable joint 203 may cause the top module 101 to collapse. In other embodiments, the top module 101 may collapse as it is forced into the opening of a catheter. In some embodiments, the catheter used for delivery and retrieving the device may have a small funnel to assist in collapsing the top module 101.

In various embodiments, the top module 101 is about 10-30 mm, 5-10 mm, 25-35 mm, or other suitable lengths.

In various embodiments, the bottom module 103 is about 10-20 mm, 5-15 mm, or 15-25 mm, or other suitable lengths.

In various embodiments, the top module 101, and/or bottom module 103 is self-expandable or balloon expandable. Examples of self-expandable valves include, but are not limited to, MEDTRONIC COREVALVE, which is constructed with a nitinol self-expanding valve stent frame and porcine pericardial leaflets. Examples of balloon-expandable valves include, but are not limited to, EDWARDS SAPIEN XT valve, which is constructed with a cobalt-chromium balloon-expandable valve stent frame and bovine pericardial leaflets.

In some embodiments, the device can comprise a nitinol frame or other suitable materials. Many other examples of such materials are described in U.S. Publication No. US2011/0319989, incorporated by reference herein in their entirety. The top module 101 may be a stent, or a structure that is comprised of various combinations of supporting ribs or wires that aid in orientation of the device to replace a patient's valve. In various embodiments, the top module 101 and/or the bottom module 103 comprises a nitinol frame, or other suitable materials as described herein. The bottom module 103 may be a replacement valve that includes a stent or other structure for fixing the bottom module 103 to the aortic canal.

In various embodiments, the bottom module 103 is configured to replace either an aortic valve, a mitral valve, a pulmonary valve, or a tricuspid valve. In various embodiments, the orientation of the top 101 and bottom 103 modules may switch depending on the access approach employed for device delivery (for instance, transfemoral or transapical). In various embodiments, the replacement heart valve contained in the bottom module 103 is a prosthetic valve or a bio-prosthetic valve. In some embodiments, a prosthetic valve is made of purely artificial or non-biological materials and a bioprosthetic valve is made of animal tissues alone or in combination with artificial or non-biological materials.

In various embodiments, the top module 101 is mechanically attached to the bottom module 103 prior to deployment of the device. In various embodiments, the top module 101 is mechanically detached from the bottom module 103 after deployment of the device by unlocking a detachable joint 203. Examples of mechanical detachment mechanisms are shown in U.S. Pat. Nos. 5,250,071 and 5,354,295, each of which is incorporated herein by reference in its entirety. For instance, detachable joint 203 may be interlocking clasps that attach the top and bottom modules and are connected to control wires 201 within the catheter. Retraction of the control wire 201 uncouples the detachable joint 203 and therefore separates the top 101 and bottom modules 103 allowing them to separate and the top module 101 to be retrieved. Other mechanical joints 203 that detach may be utilized, including clasp and ring, with a clasp on one module and a ring on the other module, and others.

In various embodiments, the top module 101 may be electrolytically detached from the bottom module 103 after deployment of the device. In various embodiments, the top module 101 is attached to the bottom module 103 through an electrolytically severable joint 203 prior to deployment of the device. The electrolytically severable joint 203 may be severed after deployment of the device. Examples of electrolytically severable joints 203 include but are not limited to those use in electrically detachable coils (Zubillaga et al., Endovascular occlusion of intracranial aneurysms with electrically detachable coils: correlation of aneurysm neck size and treatment results; AJNR *Am J Neuroradiol*. 1994 May; 15(5):815-20). Electrolytically severable joints are a type of sacrificial link between a therapeutic device which is delivered into a patient's body and is intended to remain at the desired location (e.g., the bottom module 103) and another delivery device which is used to deliver the therapeutic device (e.g., the top module 101). An electrical current is applied to this type of joints 203 to electrolytically separate the two devices linked together by these joints 203. For example, in some embodiments, a portion of the link or joint 203 will be stainless steel and will be exposed to the bloodstream. Once the device has been implanted and is in place, positive current may be applied to the exposed portion to corrode away the stainless steel and separating the top module 101 from the bottom module 103. In some embodiments, this will be after applying current for a few minutes. In this embodiment, certain portions of the joint 203 or surrounding material that are not to be degraded are coated with an insulation coating, for example polyethylene, to prevent their degradation while allowing the exposed portion to degrade and the top module 103 to detach. To apply current, a wire connected to an external power source may be fed into the patient and connected to the exposed stainless steel portion. In other embodiments, a catheter or guide wire may include a battery or other power source embedded within it. In still other embodiments, a series or parallel combination of wires and conductors may carry the electric current to the exposed portion for corrosion. Construction of effective electrolytic joints 203 and mechanisms for applying power to the joints 203 will be apparent for a person of skill in the art, for examples as described in U.S. Pat. Nos. 5,122,136, 5,354,295, 5,423,829, 5,964,797, 6,589,230, 6,953,473 and 8,377,112, which are herein incorporated by reference in their entirety.

In various embodiments, provided herein are methods for transcatheter valve replacement. The method comprise the following steps: (1) providing a device, comprising a top module 101 and a bottom module 103, wherein the bottom module 103 comprises a replacement heart valve, the top module 101 is attached to the bottom module 103 prior to deployment of the device; (2) deploying the device in a patient's heart to replace a diseased heart valve; (3) detaching the top module 101 from the bottom module 103; and (4) retrieving the top module 101 out of the patient's heart. In some embodiments, the top module 101 is electrolytically or mechanically, or by other electronic means, detached from the bottom module 103 after deployment of the device.

Also in accordance with the present invention, as TAVR is a known surgical procedure, one of ordinary skill in the art would readily recognize that the method could involve other additional steps, which are not described in details here. These additional steps include, but are not limited to, anesthesia, sterilization, heparinization, accessing the patient's heart via various routes such as femoral, transaortic, transapical, transaxillary, subclavian, transseptal and transcaval approaches, ventricular pacing, stitching of the access site or percutaneous femoral closure.

Devices with Bio-Absorbable Top Modules

In various embodiments, provided herein is a device for transcatheter valve replacement. The device comprises a top module 101 and a bottom module 103. The bottom module 103 includes a replacement heart valve. The top module 101 is made of bio-absorbable material and is attached to the bottom module 103 prior to deployment of the device. Examples of bio-absorbable materials include, but are not limited to, magnesium alloy, poly-L-lactic acid (PLLA), PLLA coated with poly-D, L-lactide, salicylate molecules, or absorbable tyrosine-derived polycarbonate polymer, or a combination thereof. Additional details may be found in Ormiston et al., (Bioabsorbable Coronary Stents, Circ Cardiovasc Interv. 2009; 2:255-2600), herein incorporated by reference in its entirety.

In various embodiments, the top module 101 is about 10-30 mm in length. In various embodiments, the bottom module 103 is about 10-20 mm in length.

In various embodiments, the device is self-expandable or balloon expandable. Examples of self-expandable valves include, but are not limited to, MEDTRONIC COREVALVE, which is constructed with a nitinol self-expanding valve stent frame and porcine pericardial leaflets. Examples of balloon-expandable valves include, but are not limited to, EDWARDS SAPIEN XT valve, which is constructed with a cobalt-chromium balloon-expandable valve stent frame and bovine pericardial leaflets.

The device can comprise a nitinol or alternative metallic alloy frame. In various embodiments, the top module 101 comprises a nitinol, stainless steel, platinum-iridium, magnesium or cobalt-chromium frame. In various embodiments, the bottom module 103 comprises a nitinol, stainless steel, platinum-iridium, magnesium or cobalt-chromium frame, or other materials as disclosed herein or known in the art.

In various embodiments, wherein the bottom module 103 is configured to replace aortic valve, mitral valve, pulmonary valve, or tricuspid valve. In various embodiments, the replacement heart valve is a prosthetic valve or a bioprosthetic valve. In some embodiments, a prosthetic valve is made of purely artificial or non-biological materials, and a bioprosthetic valve is made of animal tissues alone or in combination with artificial or non-biological materials.

In various embodiments, the top module 101 comprises magnesium alloy, poly-L-lactic acid (PLLA), PLLA coated with poly-D, L-lactide, salicylate molecules, or absorbable tyrosine-derived polycarbonate polymer, or a combination thereof. In various embodiments, the top module 101 is absorbed about 6-12 months or 1-2 years after deployment of the device. For example, the top module 101 can be absorbed 6, 7, 8, 9, 10, 11, 12, 13, 14, 15, 16, 17, 18, 19, 20, 21, 22, 23, 24, 25, 26, 27, 28, 29, or 30 months after deployment of the device.

In various embodiments, the device further comprises radio-opaque markers. In some embodiments, the radio-opaque markers are made of gold or platinum. In other embodiments, the radio-opaque markers are iodine impregnated in bio-absorbable materials.

In various embodiments, the present invention provides for a method for transcatheter valve replacement. The method comprise the following steps: (1) providing a device, comprising a top module 101 and a bottom module 103, wherein the bottom module 103 comprises a replacement heart valve, the top module 101 is attached to the bottom module 103 prior to deployment of the device including leaflets 102, and the top module 101 is made of bio-absorbable material; and (2) deploying the device in a patient's heart to replace a diseased heart valve. In various embodiments the method for deploying the device in a patient's heart may incorporate portions of standard methods and devices for a TAVR or transapical aortic valve implantation. This may include standard guide wire and catheter delivery procedures for delivering the device. In some embodiments, the catheter delivery system may include mechanical actuators that unlock the detachable joint 203 by triggering of an electrical or mechanical switch or action, that is translated or carried down to the detachable joint 203, releasing the detachable joint. In some embodiments, a catheter/guide wire delivery system will include a retraction mechanism or guide wire that may attached to the retraction cords 201.

Also in accordance with the present invention, as TAVR is a known surgical procedure, one of ordinary skill in the art would readily recognize that the method could involve other additional steps, which are not described in details here. These additional steps include, but are not limited to, anesthesia, sterilization, heparinization, accessing the patient's heart via various routes such as femoral, transaortic and transapical approaches, ventricular pacing, and stitching of the access site or percutaneous femoral closure.

Currently, replacement valves must be a certain minimum length/height in order for them to be properly positioned during deployment. However, this length makes for a device with a surface area that is considered too large and therefore may provide too much risk of reactions, including thrombus formation. The top module 101 allows optimal positioning of the device, and is detachable or absorbable. The bottom module 103 sits in the aortic root and is short in height. The modular approach described herein allows for the valve to be of optimal length, thus leaving virtually no excess material behind after the valve replacement surgery or only temporarily leaving some excess material behind after the valve replacement surgery. This is optimal, as the extended length is only required for positioning, and is not essential once the valve is anchored in place.

In various embodiments as described in the present invention, a top module 101 first helps delivery of the replacement heart valve (e.g., the bottom module 103), and then is either detached or absorbed over time once the replacement heart valve is deployed in the subject. In the bio-absorbable version of the transcatheter valve, the top module 101 is absorbed in about 6-12 months or 1-2 years after valve deployment. In the detachable version of the transcatheter valve, the top module 101 is detached immediately or shortly after deployment of the valve, and in some embodiments, detached after a few minutes of application of positive current. This modular design is suitable for replacement of diseased aortic valves, mitral (bicuspid) valves, pulmonary valves or tricuspid valves.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A device for replacement of a heart valve comprising a top module comprising a frame and having a first width that is constant along a longitudinal axis for the entire length of the top module when in an expanded configuration; at least two retrieval cords attached to the top module; a bottom module comprising a second width equivalent to the first width, wherein the bottom module comprises a replacement heart valve; and a severable joint connecting the top module to the bottom module that is configured to release the top module from the bottom module after implantation of the bottom module.

2. The device of claim 1, wherein the top module is about 10-30 mm in length.

3. The device of claim 1, wherein the bottom module is about 10-20 mm in length.

4. The device of claim 1, wherein the bottom module is configured to replace aortic valve, mitral valve, pulmonary valve, or tricuspid valve.

5. The device of claim 1, wherein the frame comprises a nitinol or an alternative alloy.

6. The device of claim 1, wherein the bottom module comprises a nitinol or an alternative alloy frame.

7. The device of claim 1, wherein the replacement heart valve is a prosthetic valve or a bio-prosthetic valve.

8. The device of claim 1, wherein the top module is self-expandable or balloon expandable.

9. The device of claim 1, wherein the bottom module is self-expandable or balloon expandable.

10. The device of claim 1, wherein the severable joint is a mechanical release mechanism.

11. The device of claim 1, wherein the severable joint is an electrically activated mechanical release mechanism.

12. The device of claim 1, wherein the severable joint is electrolytically dissolvable through application of positive current.

13. The device of claim 1, wherein the at least two retrieval cords are made of nitinol.

* * * * *